(12) United States Patent
Repetto et al.

(10) Patent No.: US 12,017,069 B2
(45) Date of Patent: Jun. 25, 2024

(54) COCHLEAR IMPLANT SYSTEM WITH MEASUREMENT UNIT

(71) Applicant: Oticon Medical A/S, Smørum (DK)

(72) Inventors: Jean-Claude Repetto, Vallauris (FR); Pierre Stahl, Vallauris (FR)

(73) Assignee: Oticon Medical A/S, Smørum (DK)

( * ) Notice: Subject to any disclaimer, the term of this patent is extended or adjusted under 35 U.S.C. 154(b) by 312 days.

(21) Appl. No.: 17/116,702

(22) Filed: Dec. 9, 2020

(65) Prior Publication Data

US 2021/0170174 A1 Jun. 10, 2021

(30) Foreign Application Priority Data

Dec. 10, 2019 (EP) .................................. 19214824

(51) Int. Cl.
*A61N 1/05* (2006.01)
*A61N 1/08* (2006.01)
*A61N 1/36* (2006.01)
*H04R 25/00* (2006.01)

(52) U.S. Cl.
CPC ....... *A61N 1/36038* (2017.08); *A61N 1/0541* (2013.01); *A61N 1/08* (2013.01); *A61N 1/36125* (2013.01); *H04R 25/556* (2013.01); *H04R 25/558* (2013.01); *A61N 1/36142* (2013.01)

(58) Field of Classification Search
None
See application file for complete search history.

(56) References Cited

U.S. PATENT DOCUMENTS

| 7,158,825 B1 * | 1/2007 | Kroll | A61N 1/3931 607/4 |
| 2003/0204225 A1 * | 10/2003 | Heathershaw | A61N 1/36125 607/48 |
| 2012/0185015 A1 * | 7/2012 | Greenberg | A61N 1/36046 607/54 |
| 2013/0282079 A1 | 10/2013 | Kalimyer | |
| 2016/0144183 A1 | 5/2016 | Marnfeldt | |
| 2016/0235984 A1 * | 8/2016 | Karunasiri | A61N 1/36038 |
| 2017/0095667 A1 * | 4/2017 | Yakovlev | A61N 1/37235 |

* cited by examiner

*Primary Examiner* — Erica S Lee
(74) *Attorney, Agent, or Firm* — Birch, Stewart, Kolasch & Birch, LLP

(57) ABSTRACT

A cochlear implant system is disclosed. The system includes an external unit configured to receive acoustical sound and process the acoustical sound into a coded audio signal, and an implantable unit configured to receive the coded audio signal. The system further comprises a pulse generating unit configured to generate a first electrical pulse of a first pulse duration and a second electrical pulse of a second pulse duration different from the first pulse duration based on the coded audio signal. The system still further comprises an electrode array including a plurality of electrodes, wherein at least one of the plurality of electrodes is configured to receive at least the first electrical pulse and the second electrical pulse, and a capacitor connected to the at least one of the plurality of electrodes. The system still further comprises a measurement unit configured to measure, across the connection of the at least one of the plurality of electrodes and the capacitor, a first voltage based on the first electrical pulse and a second voltage based on the second electrical pulse. The system still further comprises an evaluation unit configured to calculate a voltage difference between the measured first and second voltages.

20 Claims, 7 Drawing Sheets

COCHLEAR IMPLANT SYSTEM WITH MEASUREMENT UNIT

FIELD

The present disclosure relates to a cochlear implant hearing system and a method for a cochlear implant hearing system. More particularly, the disclosure relates to such system/method provided with a measurement unit configured for testing of electrical characteristics of circuitry components, e.g. of DC blocking capacitors of cochlear implants, which related to patient safety.

BACKGROUND

Cochlear implants (CIs) are devices containing electrodes inserted in the inner ear (the cochlea) to recover the sensation of audition to people suffering from severe to profound hearing loss. CIs are bypassing most of the functional hearing chain, and generate series of electrical pulse train inside the cochlea to initiate action potentials from the hair cells. Those devices are thus mostly considered as biocompatible electronic machines. Depending on their implementation, they can be either totally implanted, either composed of two main parts. A first part is the sound processor, often placed near the ear. It contains microphones that capture the environmental sound, which is processed in real time into a series of codes usable by the second part, implanted into the patient. The implant receives both power and sound information though radiofrequency from the sound processor, and generates electrical pulses sent into the cochlea via electrodes inside the cochlea.

It is very difficult to check the implanted part of the CI system, because it is not easily accessible. The only possible method is to implement self checks. The CI contains voltage measure circuitry that can be used to check a number of voltages inside the implant, thanks to an analog to digital converter (ADC). The measurements can be transmitted outside the body via a telemetry channel. For example, this circuitry can be used to measure the impedance of the electrodes, by sending a known current into the electrode and measuring the resulting voltage. This measure is mainly used to detect any of electrode short circuit (very low impedance, implying the resistivity to be only made by the electrode leads) or open circuit (infinite impedance, implying that the current could not pass through the circuit).

To ensure electrical a patient's safety during the generation of a current pulse, any current pulse generated by the CI is counterbalanced quasi immediately with an opposite current pulse phase containing the same charge. Any unbalanced stimulation may lead to non reversible Faradaic electrochemical reactions leading to cell apoptosis. A simple representation of stimulation waveforms damaging the tissue, or not, is provided in FIG. 1.

FIG. 1 illustrates (left) stimulations that will damage the biological tissues because anodic and cathodic pulses are not balanced and illustrates (right) an electrical device that contains no error leading to safe stimulation, since anodic and cathodic pulses are balanced.

In theory, it would be possible to build a device generating perfectly balanced phases. In reality, all electrical devices are prone to errors. Some CI devices try to generate pulses as balanced as possible, but the error between anodic and cathodic phases may reach up to 10 to 15%. In order to avoid any DC component and in order to fully nullify the risks or unbalanced stimulation due to such error, CI manufacturers insert DC blocking capacitors that are able to compensate, at the end of the pulse, this difference. Some devices even send only one active pulse and use capacitors to fully discharge the active phase of the pulse, thus ensuring the full balance of the charges. FIG. 2 is depicting examples for automatic balancing from DC blocking capacitors FIG. 2 illustrates (left) realistic stimulations that contain an error on their cathodic phase, unbalancing the charges. The capacitors are used to discharge the exceeded positive or negative charge. FIG. 2 further illustrates (right) a pulse waveform using the DC blocking capacitor to ensure the full balance of the charges.

Currently, all CI manufacturers use DC blocking capacitors to ensure charge balancing (see e.g. FIG. 2). Although numbers of capacitors and the way they are attached on the CI electrodes differ between manufacturers, they share the same issue. If a DC blocking capacitor fails, the CI electrical stimulation safety is compromised. Two cases of capacitor failures can be observed. First, an open capacitor, leading to no electrical stimulation on the electrode where the capacitor is attached. Thus, the CI may become partially unusable. Second, a leaky capacitor, where electrical stimulation is still operational, but the capacitor does not play its role as a DC blocking capacitor anymore. As a result, electrical charge can be unbalanced, thus affecting a patient's safety.

Currently, there is no way to estimate a status of a capacitor (shorted or leaky capacitor) embedded into the CI. Therefore, there is a need to provide a solution that addresses at least some of the above-mentioned problems.

SUMMARY

According to an aspect of the present disclosure, a cochlear implant system is disclosed. The system includes an external unit configured to receive acoustical sound and process the acoustical sound into a coded audio signal, and an implantable unit configured to receive the coded audio signal. The system further comprises a pulse generating unit configured to generate a first electrical pulse of a first pulse duration and a second electrical pulse of a second pulse duration different from the first pulse duration based on the coded audio signal. The system still further comprises an electrode array including a plurality of electrodes, wherein at least one of the plurality of electrodes is configured to receive at least the first electrical pulse and the second electrical pulse, and a capacitor connected to the at least one of the plurality of electrodes. The system still further comprises a measurement unit configured to measure, across the connection of the at least one of the plurality of electrodes and the capacitor, a first voltage based on the first electrical pulse and a second voltage based on the second electrical pulse. The system still further comprises an evaluation unit configured to calculate a voltage difference between the measured first and second voltages.

This allows for reliably assessing a status of a capacitor in the cochlear implant system.

Furthermore, the evaluation unit of the cochlear implant system may further be configured to derive at least one type of failure of the at least one of the plurality of electrodes, the capacitor, and the connection of the at least one of the plurality of electrodes and the capacitor. The derived at least one type of failure is based on the calculated voltage difference.

This allows for further assessing in more detail the circuitry constituting the cochlear implant system.

In addition, the derived at least one type of failure is indicative of a shorted capacitor, if the calculated voltage difference is zero.

This allows for reliably identifying a shorted capacitor in the cochlear implant system.

Further, the evaluation unit cochlear implant system may further be configured to derive a capacitance value of the capacitor based on the calculated voltage difference, wherein the derived capacitance value is indicative of at least one type of failure referring to the capacitor.

Additionally, the at least one type of failure referring to the capacitor is indicative of a leaky capacitor, if the derived capacitance value exceeds a predetermined threshold value of a nominal capacitance value of the capacitor.

This allows for reliably identifying a leaky capacitor in the cochlear implant system.

Furthermore, if the derived capacitance value is equal to or below the predetermined threshold value, the evaluation unit may further be configured to derive the at least one type of failure of the at least one of the plurality of electrodes and the connection of the at least one of the plurality of electrodes and the capacitor.

This allows for still further assessing in more detail the circuitry constituting the cochlear implant system.

Moreover, the evaluation unit of the cochlear implant system may further be configured to derive a voltage relation over time comprising a relation between a duration of an electrical pulse and a voltage measured based on the electrical pulse. Still further, the evaluation unit may be configured to derive at least one type of voltage relation failure of at least one of the plurality of electrodes, the capacitor, and the connection of the at least one of the plurality of electrodes and the capacitor based on the derived voltage relation.

In addition, the at least one type of voltage relation failure is indicative of at least one of the plurality of electrodes, the capacitor, and the connection of the at least one of the plurality of electrodes and the capacitor, if the derived voltage relation over time is nonlinear over time.

This allows for assessing, in an alternative way, in more detail the circuitry constituting the cochlear implant system.

Furthermore, the capacitor of the cochlear implant system may be a DC blocking capacitor.

Additionally, the measurement unit of the cochlear implant system may further be configured to measure the first and second voltages at the end of the respective pulse duration.

Moreover, the pulse generating unit of the cochlear implant system may further be configured to select the first and second pulse durations based on a nominal time constant corresponding to the connection of the at least one of the plurality of electrodes and the capacitor.

This allows for increasing accuracy of calculated/derived values.

In addition, the pulse generating unit may further be configured to generate electrical pulses based on at least one current intensity, wherein the measurement unit is further configured to measure for each respective current intensity. Furthermore, the evaluation unit is then further configured to calculate a voltage difference for each respective current intensity, and/or to derive a capacitance value of the capacitor for each respective current intensity based on the corresponding calculated voltage difference. Additionally, the evaluation unit is then further configured to assess the at least one calculated voltage difference and/or the at least one derived capacitance value based on an error minimization method.

This further allows for increasing accuracy of calculated/derived values.

Moreover, at least one of the measurement unit and the evaluation unit of the cochlear implant system may further be configured be arranged within one or more processors, and the one or more processors are configured to be arranged within at least one of the external unit and the implantable unit.

This allows for adapting a structure of the cochlear implant system.

According to another aspect, a method for a cochlear implant system comprising an external unit receiving acoustical sound and processing the acoustical sound into a coded audio signal and an implantable unit receiving the coded audio signal is disclosed. The method comprises the steps of generating a first electrical pulse of a first pulse duration and a second electrical pulse of a second pulse duration different from the first pulse duration based on the coded audio signal. The method further comprises the steps of receiving, by at least one of a plurality of electrodes included in an electrode array, wherein the at least one of the plurality of electrodes is connected to a capacitor, at least the first electrical pulse and the second electrical pulse. The method still further comprises measuring, across the connection of the at least one of the plurality of electrodes and the capacitor, a first voltage based on the first electrical pulse and a second voltage based on the second electrical pulse. The method still further comprises calculating a voltage difference between the measured first and second voltages.

This allows for reliably assessing a status of a capacitor in the cochlear implant system.

In addition, the method may further comprise the steps of deriving at least one type of failure of at least one of the plurality of electrodes, the capacitor, and the connection of the at least one of the plurality of electrodes and the capacitor, based on the calculated voltage difference. The derived at least one type of failure is indicative of a shorted capacitor, if the calculated voltage difference is zero.

This allows for reliably identifying a shorted capacitor in the cochlear implant system.

Moreover, the method may further comprise the steps of deriving a capacitance value of the capacitor based on the calculated voltage difference, wherein the derived capacitance value may be indicative of at least one type of failure referring to the capacitor. The at least one type of failure referring to the capacitor is indicative of a leaky capacitor, if the derived capacitance value exceeds a predetermined threshold value of a nominal capacitance value of the capacitor.

Furthermore, if the derived capacitance value is equal to or below the predetermined threshold value, the method may further comprise the steps of deriving the at least one type of failure of the at least one of the plurality of electrodes and the connection of the at least one of the plurality of electrodes and the capacitor.

This allows for further assessing in more detail the circuitry constituting the cochlear implant system.

Additionally, the method may further comprise the steps of deriving a voltage relation over time comprising a relation between a duration of an electrical pulse and a voltage measured based on the electrical pulse. Still further, the method comprises the steps of deriving at least one type of voltage relation failure of at least one of the plurality of electrodes, the capacitor, and the connection of the at least one of the plurality of electrodes and the capacitor based on the derived voltage relation. Wherein if the derived voltage relation over time is nonlinear over time, the at least one type of voltage relation failure is indicative of at least one of the plurality of electrodes, the capacitor, and the connection of the at least one of the plurality of electrodes and the capacitor.

This allows for assessing, in an alternative way, in more detail the circuitry constituting the cochlear implant system.

Further, the method may comprise the steps of measuring the first and second voltages at the end of the respective pulse duration.

Moreover, the method may comprise the steps of selecting the first and second pulse durations based on a nominal time constant corresponding to the connection of the at least one of the plurality of electrodes and the capacitor.

This allows for increasing accuracy of calculated/derived values.

In addition, the method may comprise the steps of generating electrical pulses based on at least one current intensity and measuring for each respective current intensity. Further, the method then comprises calculating a voltage difference for each respective current intensity, and/or deriving a capacitance value of the capacitor for each respective current intensity based on the corresponding calculated voltage difference. Still further, the method then comprises assessing the at least one calculated voltage difference and/or the at least one derived capacitance value based on an error minimization method.

This further allows for increasing accuracy of calculated/derived values.

BRIEF DESCRIPTION OF DRAWINGS

Aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

DETAILED DESCRIPTION

Figure 1:
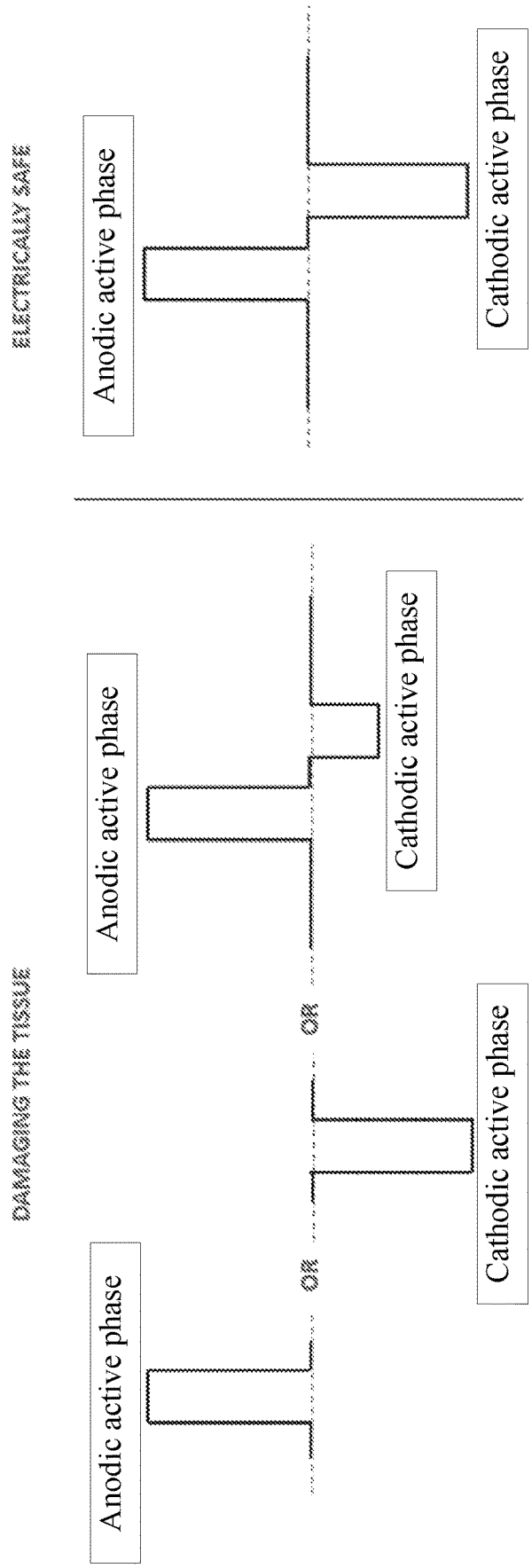
FIG. 1 illustrates (left) stimulations that will damage the biological tissues because anodic and cathodic pulses are not balanced and illustrates (right) an electrical device that contains no error leading to safe stimulation.
Figure 2:
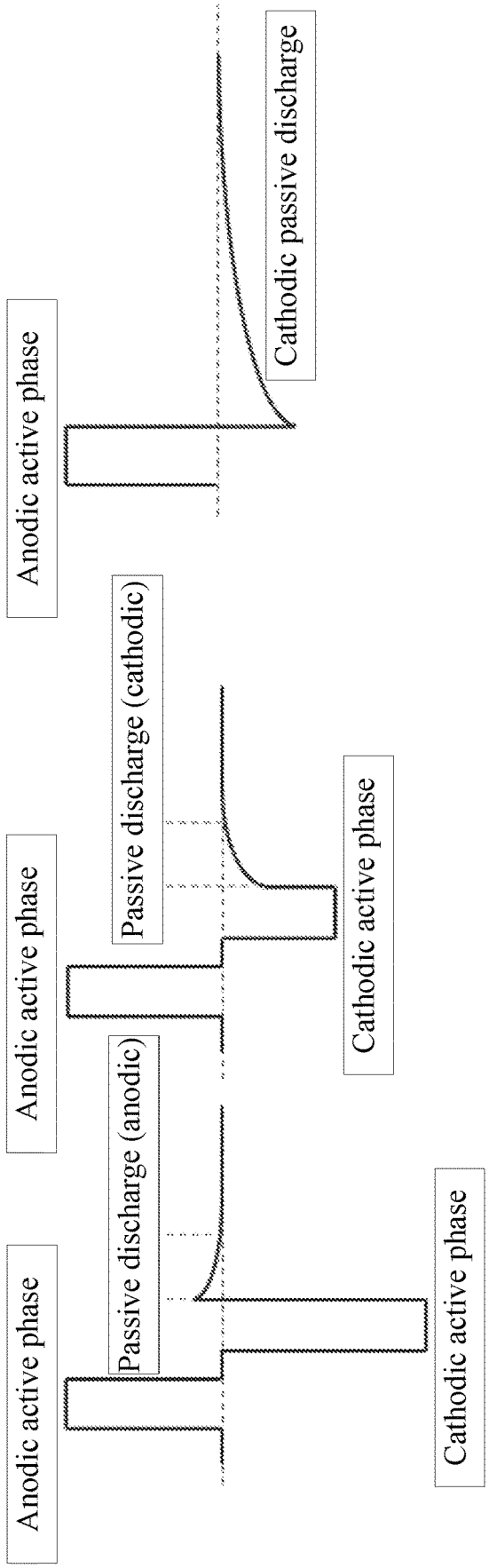
FIG. 2 illustrates (left) realistic stimulations that contain an error on their cathodic phase, unbalancing the charges, wherein the capacitors are used to discharge the exceeded positive or negative charge, and illustrates (right) a pulse waveform using the DC blocking capacitor to ensure the full balance of the charges.

The detailed description set forth below in connection with the appended drawings is intended as a description of various configurations. The detailed description includes specific details for the purpose of providing a thorough understanding of various concepts. However, it will be apparent to those skilled in the art that these concepts may be practised without these specific details. Several aspects of the apparatus and methods are described by various blocks, functional units, modules, components, circuits, steps, processes, algorithms, etc. (collectively referred to as "elements").

Depending upon particular application, design constraints or other reasons, these elements may be implemented using electronic hardware, computer program, or any combination thereof.

The electronic hardware may include microprocessors, microcontrollers, digital signal processors (DSPs), field programmable gate arrays (FPGAs), programmable logic devices (PLDs), gated logic, discrete hardware circuits, and other suitable hardware configured to perform the various functionality described throughout this disclosure. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

A hearing device may include a hearing aid that is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. The "hearing device" may further refer to a device such as an earphone or a headset adapted to receive an audio signal electronically, possibly modifying the audio signal and providing the possibly modified audio signals as an audible signal to at least one of the user's ears. Such audible signals may be provided in the form of an acoustic signal radiated into the user's outer ear, or an acoustic signal transferred as mechanical vibrations to the user's inner ears through bone structure of the user's head and/or through parts of middle ear of the user or electric signals transferred directly or indirectly to cochlear nerve and/or to auditory cortex of the user.

The hearing device is adapted to be worn in any known way. This may include i) arranging a unit of the hearing device behind the ear with a tube leading air-borne acoustic signals into the ear canal or with a receiver/loudspeaker arranged close to or in the ear canal such as in a Behind-the-Ear type hearing aid, and/or ii) arranging the hearing device entirely or partly in the pinna and/or in the ear canal of the user such as in a In-the-Ear type hearing aid or In-the-Canal/Completely-in-Canal type hearing aid, or iii) arranging a unit of the hearing device attached to a fixture implanted into the skull bone such as in Bone Anchored Hearing Aid or Cochlear Implant, or iv) arranging a unit of the hearing device as an entirely or partly implanted unit such as in Bone Anchored Hearing Aid or Cochlear Implant.

A "hearing system" refers to a system comprising one or two hearing devices, and a "binaural hearing system" refers to a system comprising two hearing devices where the devices are adapted to cooperatively provide audible signals to both of the user's ears. The hearing system or binaural hearing system may further include auxiliary device(s) that communicates with at least one hearing device, the auxiliary device affecting the operation of the hearing devices and/or benefitting from the functioning of the hearing devices. A wired or wireless communication link between the at least one hearing device and the auxiliary device is established that allows for exchanging information (e.g. control and status signals, possibly audio signals) between the at least one hearing device and the auxiliary device. Such auxiliary devices may include at least one of remote controls, remote microphones, audio gateway devices, mobile phones, public-address systems, car audio systems or music players or a combination thereof. The audio gateway is adapted to receive a multitude of audio signals such as from an entertainment device like a TV or a music player, a telephone apparatus like a mobile telephone or a computer, a PC. The audio gateway is further adapted to select and/or combine an appropriate one of the received audio signals (or combination of signals) for transmission to the at least one hearing device. The remote control is adapted to control functionality and operation of the at least one hearing devices. The function of the remote control may be implemented in a SmartPhone or other electronic device, the SmartPhone/electronic device possibly running an application that controls functionality of the at least one hearing device.

In general, a hearing device includes i) an input unit such as a microphone for receiving an acoustic signal from a user's surroundings and providing a corresponding input audio signal, and/or ii) a receiving unit for electronically receiving an input audio signal. The hearing device further includes a signal processing unit for processing the input audio signal and an output unit for providing an audible signal to the user in dependence on the processed audio signal.

The input unit may include multiple input microphones, e.g. for providing direction-dependent audio signal processing. Such directional microphone system is adapted to enhance a target acoustic source among a multitude of acoustic sources in the user's environment. In one aspect, the directional system is adapted to detect (such as adaptively detect) from which direction a particular part of the microphone signal originates. This may be achieved by using conventionally known methods. The signal processing unit may include amplifier that is adapted to apply a frequency dependent gain to the input audio signal. The signal processing unit may further be adapted to provide other relevant functionality such as compression, noise reduction, etc. The output unit may include an output transducer such as a loudspeaker/receiver for providing an air-borne acoustic signal transcutaneously or percutaneously to the skull bone or a vibrator for providing a structure-borne or liquid-borne acoustic signal. In some hearing devices, the output unit may include one or more output electrodes for providing the electric signals such as in a Cochlear Implant.

A "cochlear implant system" represents a particular type of a "hearing system" comprising an external unit, which receives acoustic sound and processes the acoustic sound into a coded audio, and an implantable unit which receives the coded audio signal.

Figure 3:
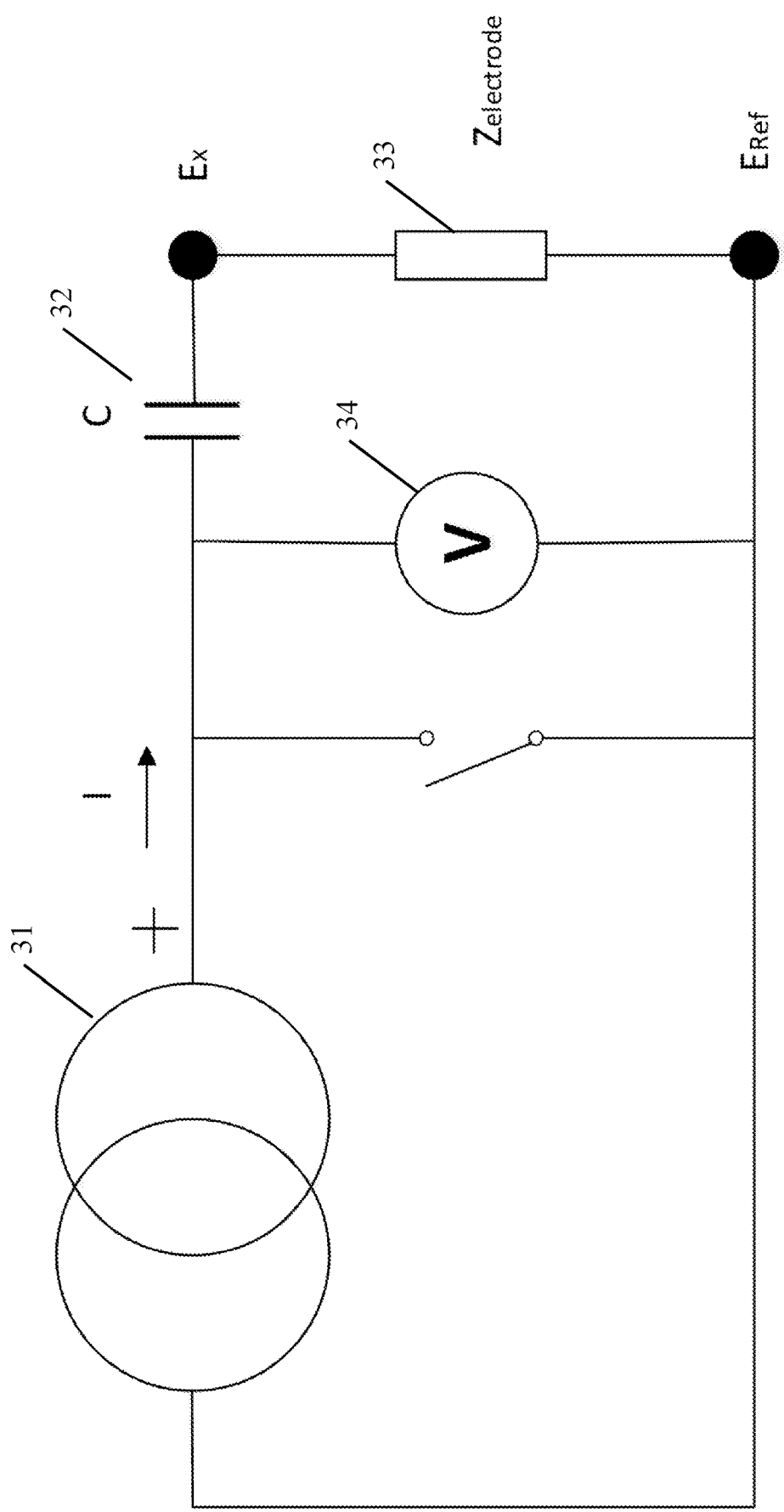
FIG. 3 illustrates a simplified diagram of an output channel of a cochlea implant system according to an embodiment of the disclosure.

Now referring to FIG. 3, it is illustrated a simplified diagram of an output channel of the implantable unit of a cochlea implant system according to an embodiment of the disclosure.

According to FIG. 3, a pulse generating unit (current source) 31 generates a current I that flows into an electrode 33 of an (not shown) electrode array through an output capacitor 32. As long as the pulse generating unit 31 is in the voltage compliance range, the current I is constant over time. Thus, a voltage V measured by a measurement unit 34 by a cochlear implant system is:

$$V(t)=I \cdot t/C+Z \cdot I,$$

where t is the time, I is the current generated by the pulse generating unit 31, C is a capacitor value, and Z is an electrode impedance.

Figure 4:
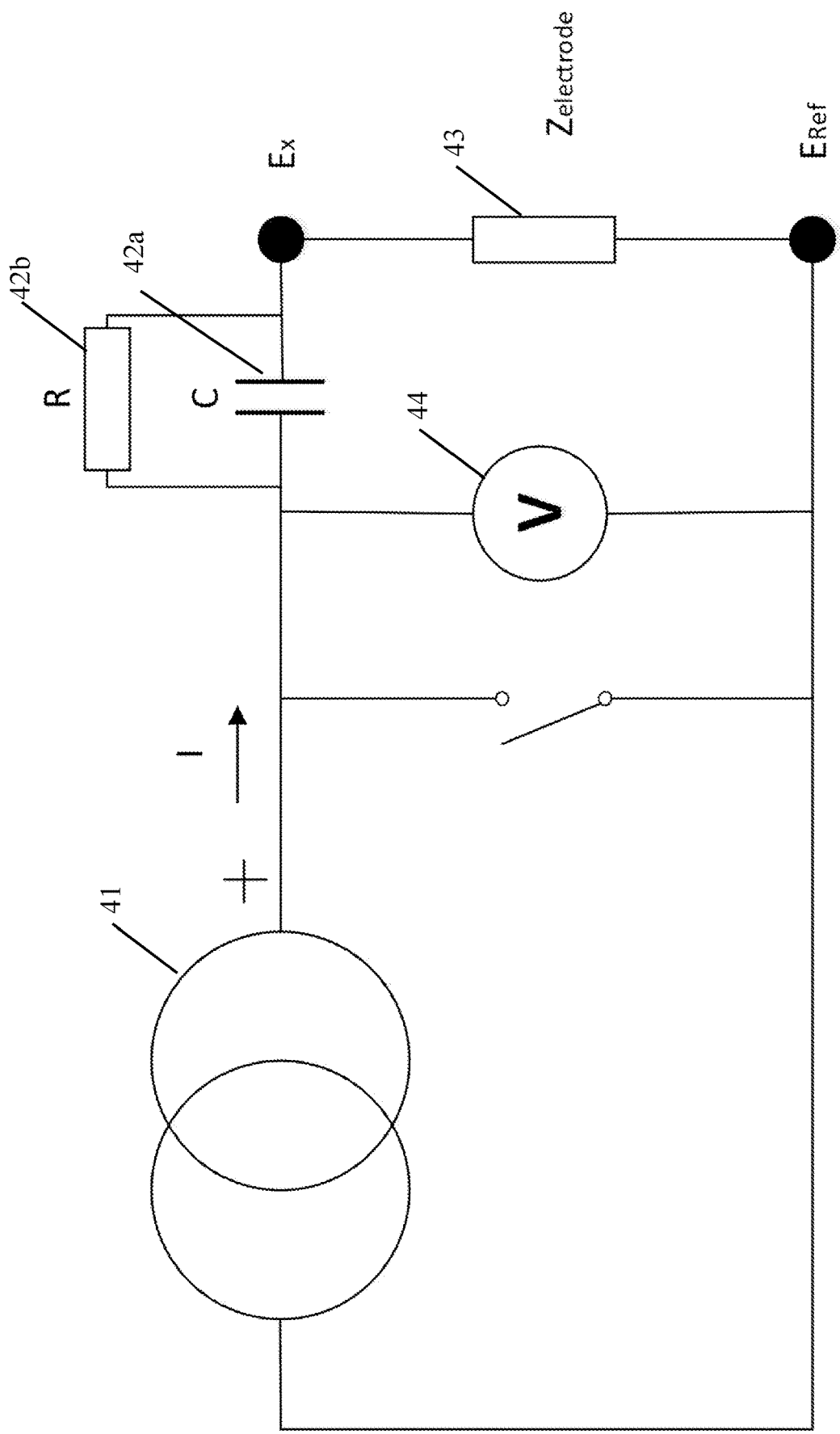
FIG. 4 illustrates a simplified diagram of an output channel comprising a leaky capacitor of a cochlea implant system according to an embodiment of the disclosure.

In case of a failure of a cochlear implant system due to a leaky capacitor, the diagram according to FIG. 3 can be modified as illustrated according to FIG. 4, where components with reference signs 41, 43, and 44 correspond to components with reference signs 31, 33, and 34 according to FIG. 3, respectively. A further description of these components is therefore omitted.

FIG. 4 illustrates a simplified diagram of the output channel comprising a leaky capacitor 42a, 42b of the implantable unit of the cochlea implant system according to an embodiment of the disclosure.

In this case, according to FIG. 4, a voltage V measured by the measurement unit 44 by the cochlear implant system is modified to become:

$$V(t)=R \cdot I \cdot (1-e^{-t/R \cdot C})+Z \cdot I,$$

where t is the time, I is the current generated by the pulse generating unit 41, C is the capacitor value, Z is the electrode impedance, and R is the leak resistance.

Figure 5:
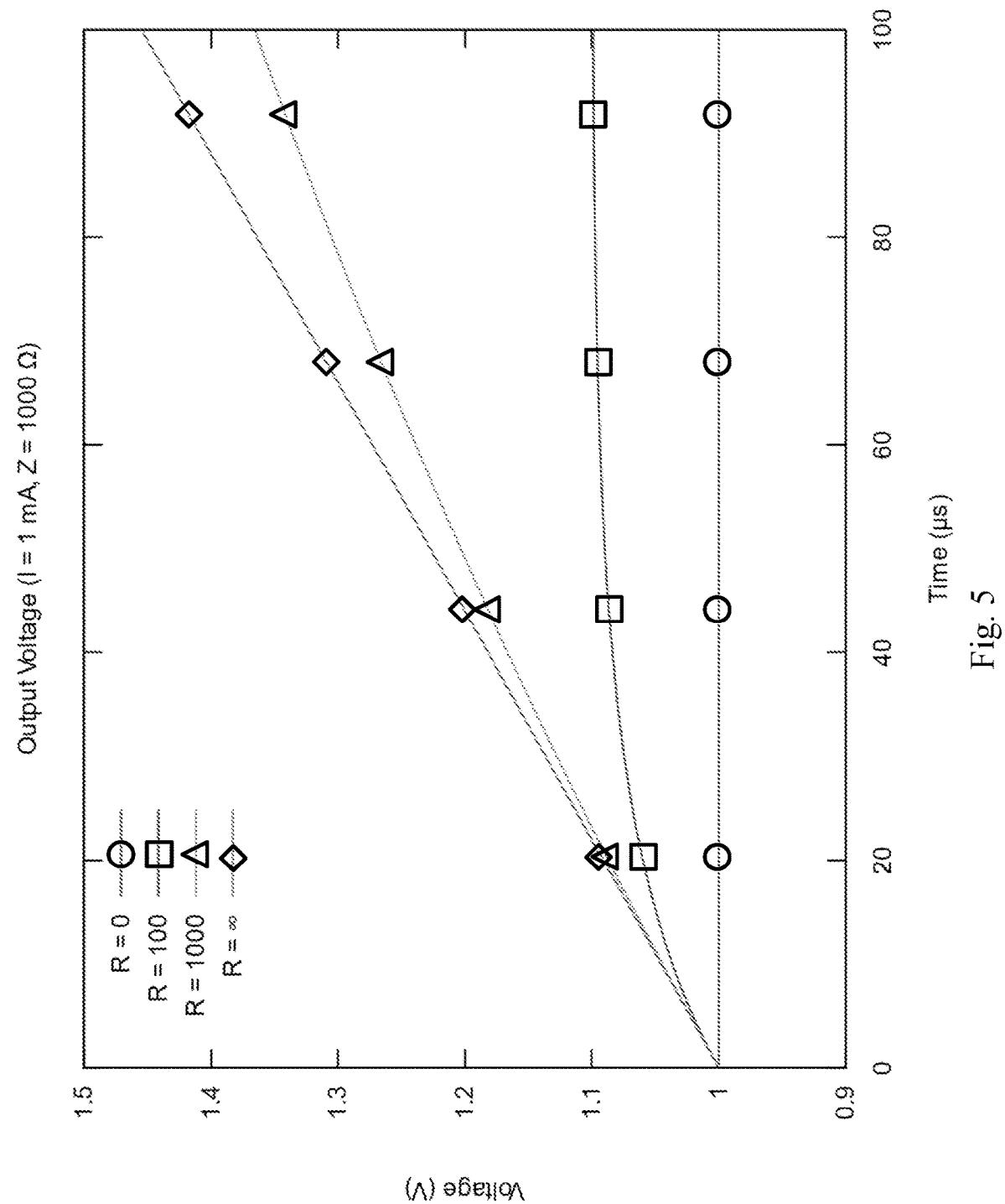
FIG. 5 illustrates a diagram showing relations of an output voltage measured by a cochlear implant over time for different leak values of a capacitor according to an embodiment of the disclosure.

Thus, the output voltage with the leaky capacitor 42a, 42b appears to be lower than in a case with a non-leaky capacitor 32, and is nonlinear over time, as detailed in FIG. 5.

Namely, according to FIG. 5, it is illustrated a diagram showing relations of an output voltage measured by a measurement unit 34, 44 by a cochlear implant system over time for different leak values of a capacitor 32, 42a, 42b according to an embodiment of the disclosure.

Specifically, a linear behavior of the measured voltage over time is identified for an infinite leak resistance (R=∞), wherein a nonlinear behavior deviates the more from the linear behavior, the lower the leak resistance R is (see R=100 and R=1000 in FIG. 5). No voltage variations over time occur for a leak resistance of zero (R=0).

Therefore, stimulating the electrode 33, 43 with two different pulse lengths $(T_1, T_2)$ will obtain two voltage measurements $(VT_1, VT_2)$:

$$VT_1=I \cdot T_1/C+Z \cdot I$$

$$VT_2=I \cdot T_2/C+Z \cdot I$$

Furthermore, by calculating the difference of the two voltage measurements, the Z component is removed from the equation and an estimation of the capacitor value can be calculated by:

$$C=I \cdot (T_1-T_2)/(VT_1-VT_2)$$

Consequently, if the result is significantly higher than the nominal capacitor value, taking into account the measure errors, it proves that the capacitor is leaky (leaky capacitor 42a, 42b). If $VT_1$ and $VT_2$ are equal, the capacitor is shorted.

Figure 6:
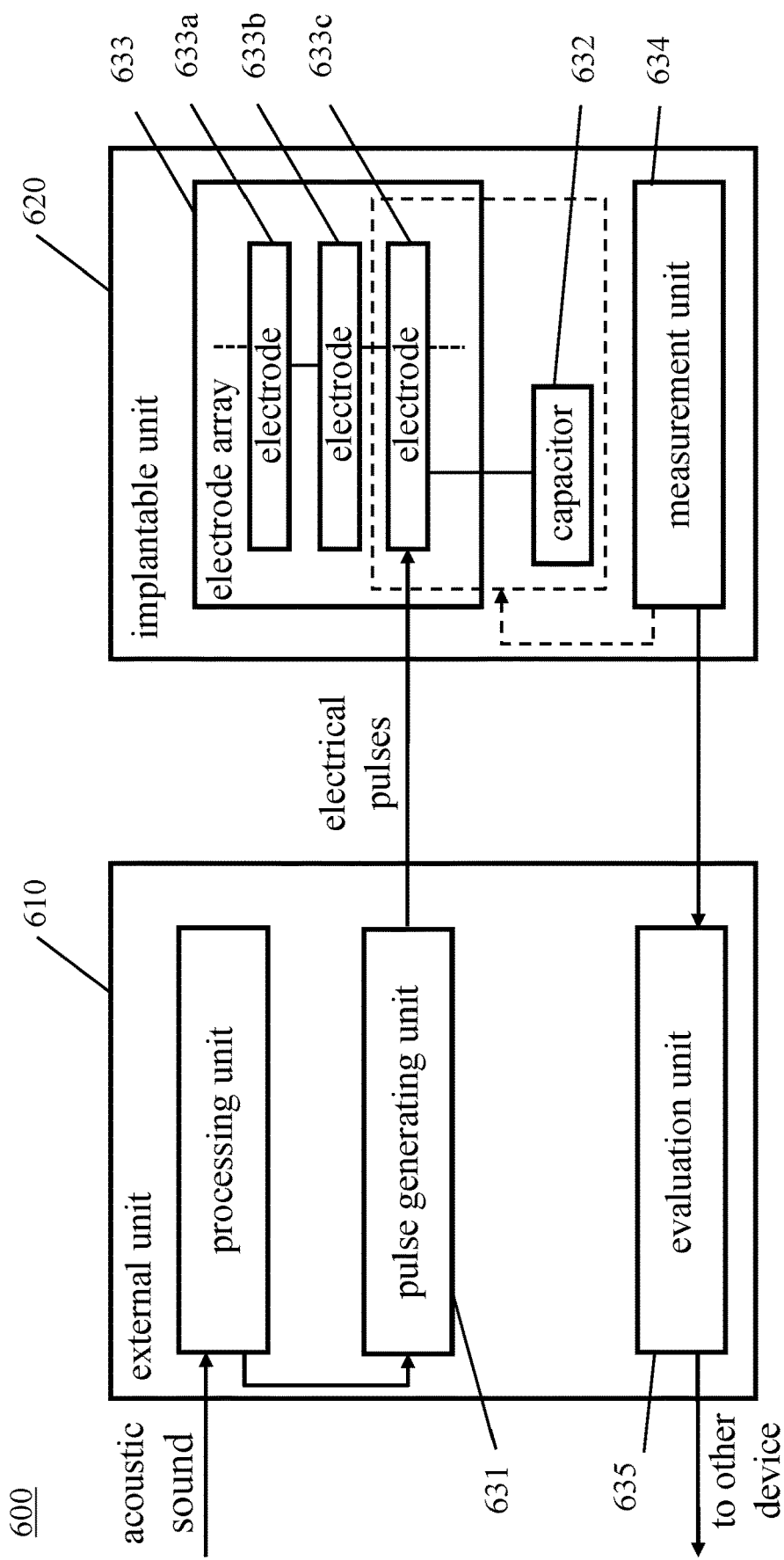
FIG. 6 illustrates a cochlear implant system according to an embodiment of the disclosure.

Now, in the light of the above, referring to FIG. 6, which illustrates a cochlear implant system 600 according to an aspect of the disclosure.

According to FIG. 6, the electrode array 633 is arranged in the implantable unit 620. Specifically, the electrode array 633 is positioned within the cochlea of a recipient, and the electrode array 633 provides stimulation to the auditory nerves of the cochlear of the recipient. The hair cells within the cochlear starts to move, and signals are generated and transmitted through the auditory nerves to the brain of the recipient. The brain translates the signals into an acoustic sound which can be perceived and understood by the recipient.

Further, according to the schematic diagram illustrated in FIG. 6, the cochlear implant system 600 includes an external unit 610 configured to receive acoustical sound and process the acoustical sound into a coded audio signal, and an implantable unit 620 configured to receive the coded audio signal. The system 600 further comprises a pulse generating unit 631 configured to generate a first electrical pulse of a first pulse duration and a second electrical pulse of a second pulse duration different from the first pulse duration based on the coded audio signal. The system 600 still further comprises an electrode array 633 including a plurality of electrodes 633a, 633b, 633c, wherein at least one of the plurality of electrodes 633c is configured to receive at least the first electrical pulse and the second electrical pulse, and a capacitor 632 connected to the at least one of the plurality of electrodes 633c. The system 600 still further comprises a measurement unit 634 configured to measure, across the connection of the at least one of the plurality of electrodes 633c and the capacitor 632, a first voltage based on the first electrical pulse and a second voltage based on the second electrical pulse. The system 600 still further comprises an evaluation unit 635 configured to calculate a voltage difference between the measured first and second voltages.

It is to be noted that the components with reference signs 631, 632, 633 (633a, 633b, 633c), and 634 correspond to components with reference signs 31, 32, 33, and 34 according to FIG. 3, respectively. It is further to be noted that the evaluation unit 635 may be arranged to be comprised by the implantable unit 620. In addition, the evaluation unit 635 may be arranged to be part of the measurement unit 634, thus being comprised by the implantable unit 620. Furthermore, an evaluation result obtained by the evaluation unit 635 may be transmitted to other devices. Still further, data output by the evaluation unit 635 may be further evaluated by other devices.

According to various exemplary embodiments, the evaluation unit 635 of the cochlear implant system 600 may further be configured to derive at least one type of failure of the at least one of the plurality of electrodes 633c, the capacitor 632, and the connection of the at least one of the plurality of electrodes 633c and the capacitor 632. The derived at least one type of failure is based on the calculated voltage difference.

This allows for further assessing in more detail the circuitry constituting the cochlear implant system 600.

At least according to some exemplary embodiments, the derived at least one type of failure is indicative of a shorted capacitor 632, if the calculated voltage difference is zero.

This allows for reliably identifying a shorted capacitor 632 in the cochlear implant system 600.

According to various exemplary embodiments, the evaluation unit 635 of the cochlear implant system 600 may further be configured to derive a capacitance value of the capacitor 632 based on the calculated voltage difference, wherein the derived capacitance value is indicative of at least one type of failure referring to the capacitor 632.

Additionally, according to at least some exemplary embodiments, the at least one type of failure referring to the capacitor 632 is indicative of a leaky capacitor 632, if the derived capacitance value exceeds a predetermined threshold value of a nominal capacitance value of the capacitor 632.

This allows for reliably identifying a leaky capacitor 632 in the cochlear implant system 600.

Furthermore, according to various exemplary embodiments, if the derived capacitance value is equal to or below the predetermined threshold value, the evaluation unit 635 may further be configured to derive the at least one type of failure of the at least one of the plurality of electrodes 633c and the connection of the at least one of the plurality of electrodes 633c and the capacitor 632.

This allows for still further assessing in more detail the circuitry constituting the cochlear implant system 600.

Moreover, according to various exemplary embodiments, the evaluation unit 635 of the cochlear implant system 600 may further be configured to derive a voltage relation over time comprising a relation between a duration of an electrical pulse and a voltage measured based on the electrical pulse. Still further, the evaluation unit 635 is then configured to derive at least one type of voltage relation failure of at least one of the plurality of electrodes 633c, the capacitor 632, and the connection of the at least one of the plurality of electrodes 633c and the capacitor 632 based on the derived voltage relation.

In addition, according to at least some exemplary embodiments, the at least one type of voltage relation failure is indicative of at least one of the plurality of electrodes 633c, the capacitor 632, and the connection of the at least one of the plurality of electrodes 633c and the capacitor 632, if the derived voltage relation over time is nonlinear over time.

This allows for assessing, in an alternative way, in more detail the circuitry constituting the cochlear implant system 600.

Furthermore, according to various exemplary embodiments, the capacitor 632 of the cochlear implant system 600 may be a DC blocking capacitor.

Additionally, according to various exemplary embodiments, the measurement unit 634 of the cochlear implant system 600 may further be configured to measure the first and second voltages at the end of the respective pulse duration.

Moreover, according to at least some exemplary embodiments, the pulse generating unit 631 of the cochlear implant system 600 may further be configured to select the first and second pulse durations based on a nominal time constant corresponding to the connection of the at least one of the plurality of electrodes 633c and the capacitor 632.

This allows for increasing accuracy of calculated/derived values.

In addition, according to various exemplary embodiments, the pulse generating unit 631 may further be configured to generate electrical pulses based on at least one current intensity, wherein the measurement unit 634 is then further configured to measure for each respective current intensity. Furthermore, the evaluation unit 635 is then further configured to calculate a voltage difference for each respective current intensity, and/or to derive a capacitance value of the capacitor 632 for each respective current intensity based on the corresponding calculated voltage difference. Additionally, the evaluation unit 635 is then further configured to assess the at least one calculated voltage difference and/or the at least one derived capacitance value based on an error minimization method.

Such an error minimization method may be one of a least squares based method, an average value based method, and a rule-implemented based method.

This further allows for increasing accuracy of calculated/derived values.

Moreover, according to various exemplary embodiments, at least one of the measurement unit 634 and the evaluation unit 635 of the cochlear implant system 600 may further be configured be arranged within one or more processors, and the one or more processors may be configured to be arranged within at least one of the external unit 610 and the implantable unit 620.

This allows for adapting a structure of the cochlear implant system 600.

Figure 7:
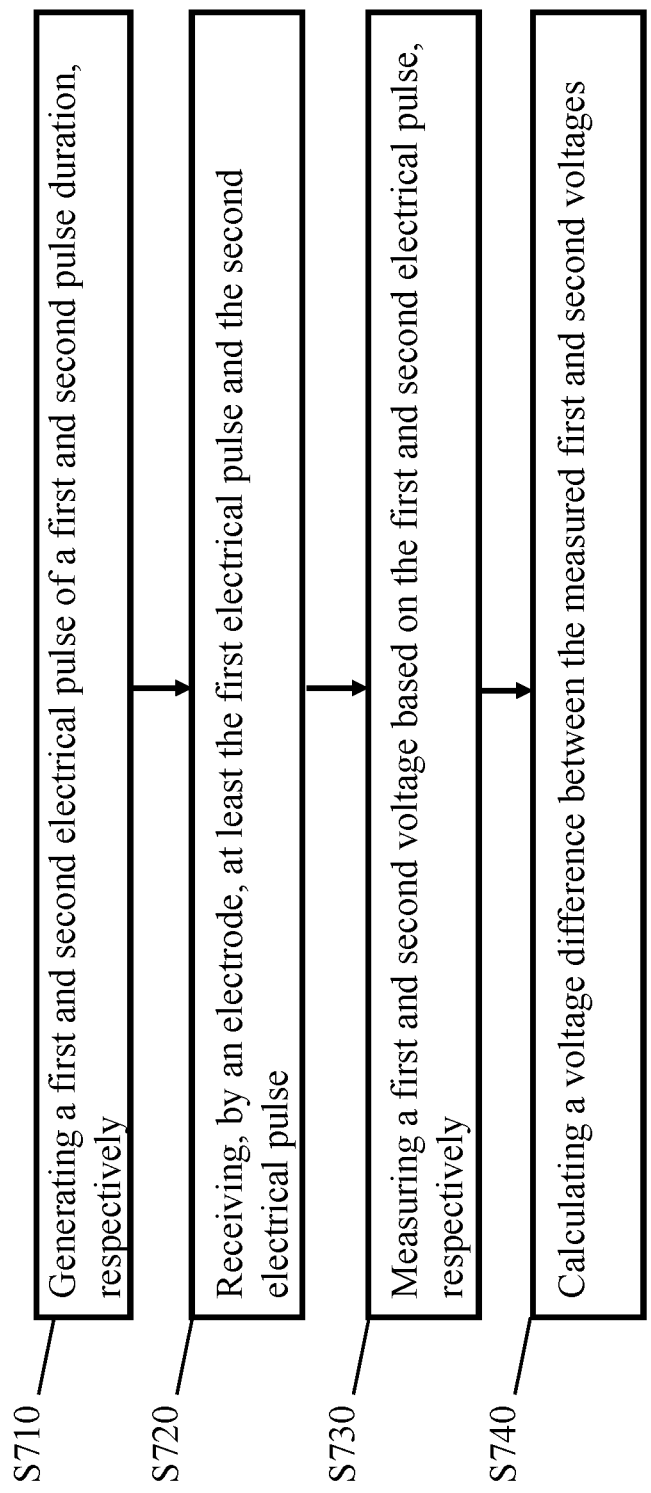
FIG. 7 illustrates a method for a cochlear implant system according to an embodiment of the disclosure.

FIG. 7 illustrates a method for a cochlear implant system according to another aspect of the disclosure. The method according to FIG. 7 may be executed by the cochlear implant system 600 according to FIG. 6, but is not limited thereto. Further, the cochlear implant system 600 according to FIG. 6 may execute the method according to FIG. 7, but is not limited thereto.

Specifically, according to FIG. 7, a method for a cochlear implant system 600 comprising an external unit 610 receiving acoustical sound and processing the acoustical sound into a coded audio signal and an implantable unit 620 receiving the coded audio signal is disclosed. The method comprises the steps of generating (Step S710) a first electrical pulse of a first pulse duration and a second electrical pulse of a second pulse duration different from the first pulse duration based on the coded audio signal. The method further comprises the steps of receiving (Step S720), by at least one of a plurality of electrodes 633a, 633b, 633c included in an electrode array 633, wherein the at least one of the plurality of electrodes 633c is connected to a capacitor 632, at least the first electrical pulse and the second electrical pulse. The method still further comprises measuring (Step S730), across the connection of the at least one of the plurality of electrodes 633c and the capacitor 632, a first voltage based on the first electrical pulse and a second voltage based on the second electrical pulse. The method still further comprises calculating (Step S740) a voltage difference between the measured first and second voltages.

This allows for a method for reliably assessing a status of a capacitor 632 in the cochlear implant system 600.

In addition, according to various exemplary embodiments, the method may further comprise the steps of deriving at least one type of failure of at least one of the plurality of electrodes 633c, the capacitor 632, and the connection of the at least one of the plurality of electrodes 633c and the capacitor 632, based on the calculated voltage difference. The derived at least one type of failure is indicative of a shorted capacitor 632, if the calculated voltage difference is zero.

This allows for a method for reliably identifying a shorted capacitor 632 in the cochlear implant system 600.

Moreover, according to at least some exemplary embodiments, the method may further comprise the steps of deriving a capacitance value of the capacitor 632 based on the calculated voltage difference, wherein the derived capacitance value may be indicative of at least one type of failure referring to the capacitor 632. The at least one type of failure referring to the capacitor 632 is indicative of a leaky capacitor 632, if the derived capacitance value exceeds a predetermined threshold value of a nominal capacitance value of the capacitor 632.

Furthermore, according to various exemplary embodiments, if the derived capacitance value is equal to or below the predetermined threshold value, the method may further comprise the steps of deriving the at least one type of failure of the at least one of the plurality of electrodes 633c and the connection of the at least one of the plurality of electrodes 633c and the capacitor 632.

This allows for a method for further assessing in more detail the circuitry constituting the cochlear implant system 600.

Additionally, according to at least some exemplary embodiments, the method may further comprise the steps of deriving a voltage relation over time comprising a relation between a duration of an electrical pulse and a voltage measured based on the electrical pulse. Still further, the method then comprises the steps of deriving at least one type of voltage relation failure of at least one of the plurality of electrodes 633c, the capacitor 632, and the connection of the at least one of the plurality of electrodes 633c and the capacitor 632 based on the derived voltage relation. Wherein if the derived voltage relation over time is nonlinear over time, the at least one type of voltage relation failure is indicative of at least one of the plurality of electrodes 633c, the capacitor 632, and the connection of the at least one of the plurality of electrodes 633c and the capacitor 632.

This allows for a method for assessing, in an alternative way, in more detail the circuitry constituting the cochlear implant system 600.

Further, according to various exemplary embodiments, the method may comprise the steps of measuring the first and second voltages at the end of the respective pulse duration.

Moreover, according to at least some exemplary embodiments, the method may comprise the steps of selecting the first and second pulse durations based on a nominal time constant corresponding to the connection of the at least one of the plurality of electrodes 633c and the capacitor 632.

This allows for a method for increasing accuracy of calculated/derived values.

In addition, according to various exemplary embodiments, the method may comprise the steps of generating electrical pulses based on at least one current intensity and measuring for each respective current intensity. Further, the method then comprises calculating a voltage difference for each respective current intensity, and/or deriving a capacitance value of the capacitor for each respective current intensity based on the corresponding calculated voltage difference. Still further, the method then comprises assessing the at least one calculated voltage difference and/or the at least one derived capacitance value based on an error minimization method.

This further allows for a method for increasing accuracy of calculated/derived values.

A Cochlear Implant typically includes i) an external part for picking up and processing sound from the environment, and for determining sequences of pulses for stimulation of the electrodes in dependence on the current input sound, ii) a (typically wireless, e.g. inductive) communication link for simultaneously transmitting information about the stimulation sequences and for transferring energy to iii) an implanted part allowing the stimulation to be generated and applied to a number of electrodes, which are implantable in different locations of the cochlea allowing a stimulation of different frequencies of the audible range. Such systems are e.g. described in U.S. Pat. No. 4,207,441 and in U.S. Pat. No. 4,532,930.

In an aspect, the hearing device comprises multi-electrode array e.g. in the form of a carrier comprising a multitude of electrodes adapted for being located in the cochlea in proximity of an auditory nerve of the user. The carrier is preferably made of a flexible material to allow proper positioning of the electrodes in the cochlea such that the electrodes may be inserted in cochlea of a recipient. Preferably, the individual electrodes are spatially distributed along the length of the carrier to provide a corresponding spatial distribution along the cochlear nerve in cochlea when the carrier is inserted in cochlea.

In still a further aspect, the functions may be stored on or encoded as one or more instructions or code on a tangible computer-readable medium. The computer readable medium includes computer storage media adapted to store a computer program comprising program codes, which when run on a processing system causes the data processing system to perform at least some (such as a majority or all) of the steps of the method described above, in the and in the claims.

The above described method, including all corresponding exemplary embodiments, for a cochlear implant system may be implemented in software.

By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media. In addition to being stored on a tangible medium, the computer program can also be transmitted via a transmission medium such as a wired or wireless link or a network, e.g. the Internet, and loaded into a data processing system for being executed at a location different from that of the tangible medium.

In another aspect, a data processing system is disclosed comprising a processor adapted to execute the computer program for causing the processor to perform at least some (such as a majority or all) of the steps of the method described above and in the claims.

As already outlined above, the above described method, including all corresponding exemplary embodiments, for a cochlear implant system may be implemented in software.

It is intended that the structural features of the devices described above, either in the detailed description and/or in the claims, may be combined with steps of the method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening elements may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. A cochlear implant system, comprising:
   an external unit configured to receive acoustical sound and process the acoustical sound into a coded audio signal,
   an implantable unit configured to receive the coded audio signal,
   a pulse generating unit configured to generate a first electrical pulse of a first pulse duration and a second electrical pulse of a second pulse duration different from the first pulse duration based on the coded audio signal,
   an electrode array including a plurality of electrodes, wherein at least one of the plurality of electrodes is configured to receive at least the first electrical pulse and the second electrical pulse,
   a capacitor connected to the at least one of the plurality of electrodes,
   a measurement unit configured to measure, across the connection of the at least one of the plurality of electrodes and the capacitor, a first voltage based on the first electrical pulse and a second voltage based on the second electrical pulse, and
   an evaluation unit configured to calculate a voltage difference between the measured first and second voltages, wherein:
   the evaluation unit is further configured to derive a capacitance value of the capacitor based on the calculated voltage difference, and
   the derived capacitance value is indicative of at least one type of failure referring to the capacitor,
   wherein the derived at least one type of failure is indicative of a shorted capacitor if the calculated voltage difference is zero.

2. The cochlear implant system according to claim 1, wherein
   the at least one type of failure referring to the capacitor is indicative of a leaky capacitor, if the derived capacitance value exceeds a predetermined threshold value of a nominal capacitance value of the capacitor.

3. The cochlear implant system according to claim 2, wherein
   if the derived capacitance value is equal to or below the predetermined threshold value,
   the evaluation unit is further configured to derive the at least one type of failure of the at least one of the plurality of electrodes and the connection of the at least one of the plurality of electrodes and the capacitor.

4. The cochlear implant system according to claim 1, wherein the evaluation unit is further configured to derive a voltage relation over time comprising a relation between a duration of an electrical pulse and a voltage measured based on the electrical pulse, and derive at least one type of voltage relation failure of the capacitor based on the derived voltage relation.

5. The cochlear implant system according to claim 4, wherein the at least one type of voltage relation failure is indicative of the capacitor if the derived voltage relation over time is nonlinear over time.

6. The cochlear implant system according to claim 1, wherein the capacitor is a DC blocking capacitor.

7. The cochlear implant system according to claim 1, wherein the measurement unit is further configured to measure the first and second voltages at the end of the respective pulse duration.

8. The cochlear implant system according to claim 1, wherein the pulse generating unit is further configured to select the first and second pulse durations based on a nominal time constant corresponding to the connection of the at least one of the plurality of electrodes and the capacitor.

9. The cochlear implant system according to claim 1, wherein:

the pulse generating unit is further configured to generate electrical pulses based on at least one current intensity, the measurement unit is further configured to measure for each respective current intensity, the first voltage and the second voltage, and the evaluation unit is further configured to:

calculate a voltage difference for each respective current intensity, and/or derive a capacitance value of the capacitor for each respective current intensity based on the corresponding calculated voltage difference, wherein the evaluation unit is further configured to assess the at least one calculated voltage difference and/or the at least one derived capacitance value based on an error minimization method.

10. The cochlear implant system according to claim 1, wherein at least one of the measurement unit and the evaluation unit is further configured be arranged within one or more processors, and the one or more processors are configured to be arranged within at least one of the external unit and the implantable unit.

11. The cochlear implant system according to claim 1, wherein the derived capacitance value is calculated independent of electrode impedance.

12. A method for a cochlear implant system comprising an external unit receiving acoustical sound and processing the acoustical sound into a coded audio signal and an implantable unit receiving the coded audio signal, the method comprises the steps of generating a first electrical pulse of a first pulse duration and a second electrical pulse of a second pulse duration different from the first pulse duration based on the coded audio signal, receiving, by at least one of a plurality of electrodes included in an electrode array, wherein the at least one of the plurality of electrodes is connected to a capacitor, at least the first electrical pulse and the second electrical pulse, measuring, across the connection of the at least one of the plurality of electrodes and the capacitor, a first voltage based on the first electrical pulse and a second voltage based on the second electrical pulse, calculating a voltage difference between the measured first and second voltages, wherein the method further comprises deriving a capacitance value of the capacitor based on the calculated voltage difference, evaluating the capacitor based on the derived capacitance value, the derived capacitance value being indicative of at least one type of capacitor failure deriving a voltage relation over time comprising a relation between a duration of an electrical pulse and a voltage measured based on the electrical pulse, and deriving at least one type of voltage relation failure of the capacitor based on the derived voltage relation, wherein if the derived voltage relation over time is nonlinear over time, the at least one type of voltage relation failure is indicative of the capacitor.

13. The method for a cochlear implant system according to claim 12, wherein the method further comprises:

determining whether the calculated voltage difference is zero; and in accordance with a determination that the calculated voltage difference is zero, evaluating the capacitor as being a shorted capacitor.

14. The method for a cochlear implant system according to claim 13, wherein the method further comprises:

determining whether the derived capacitance value exceeds a predetermined threshold value of a nominal capacitance value of the capacitor; and in accordance with a determination that the derived capacitance value exceeds a predetermined threshold value of a nominal capacitance value of the capacitor, evaluating the capacitor as being a leaky capacitor.

15. The method for a cochlear implant system according to claim 14, wherein the method further comprises:

determining whether the derived capacitance value is equal to or below the predetermined threshold value; and in accordance with a determination that the derived capacitance value is equal to or below the predetermined threshold value:

deriving the at least one type of failure of the at least one of the plurality of electrodes and the connection of the at least one of the plurality of electrodes and the capacitor.

16. The method for a cochlear implant system according to claim 12, further comprising the steps of measuring the first and second voltages at the end of the respective pulse duration.

17. The method for a cochlear implant system according to claim 12, further comprising the steps of selecting the first and second pulse durations based on a nominal time constant corresponding to the connection of the at least one of the plurality of electrodes and the capacitor.

18. The method for a cochlear implant system according to claim 12, further comprising the steps of generating electrical pulses based on at least one current intensity, measuring, for each respective current intensity, the first voltage and the second voltage, calculating the voltage difference of the first voltage and the second voltage for each respective current intensity, and deriving the capacitance value of the capacitor for each respective current intensity based on the corresponding calculated voltage difference for each respective current intensity, and assessing the voltage difference and the capacitance value based on an error minimization method.

19. The method for a cochlear implant system according to claim 12, wherein the derived capacitance value is calculated independent of electrode impedance.

20. A cochlear implant system, comprising:
an external unit configured to receive acoustical sound and process the acoustical sound into a coded audio signal,
an implantable unit configured to receive the coded audio signal,
a pulse generating unit configured to generate a first electrical pulse of a first pulse duration and a second electrical pulse of a second pulse duration different from the first pulse duration based on the coded audio signal,
an electrode array including a plurality of electrodes, wherein at least one of the plurality of electrodes is configured to receive at least the first electrical pulse and the second electrical pulse,
a capacitor connected to the at least one of the plurality of electrodes,
a measurement unit configured to measure, across the connection of the at least one of the plurality of electrodes and the capacitor, a first voltage based on the first electrical pulse and a second voltage based on the second electrical pulse, and
an evaluation unit configured to calculate a voltage difference between the measured first and second voltages, and wherein the evaluation unit is further configured to:
   derive a capacitance value of the capacitor based on the calculated voltage difference,
   the derived capacitance value is indicative of at least one type of failure referring to the capacitor,
   derive a voltage relation over time comprising a relation between a duration of an electrical pulse and a voltage measured based on the electrical pulse, and
   derive at least one type of voltage relation failure of the capacitor based on the derived voltage relation.

* * * * *

UNITED STATES PATENT AND TRADEMARK OFFICE
CERTIFICATE OF CORRECTION

PATENT NO. : 12,017,069 B2
APPLICATION NO. : 17/116702
DATED : June 25, 2024
INVENTOR(S) : Jean-Claude Repetto and Pierre Stahl Page 1 of 1

It is certified that error appears in the above-identified patent and that said Letters Patent is hereby corrected as shown below:

In the Claims

Claim 12, Column 16, Line 8, please replace "at least one type of capacitor failure" with --at least one type of capacitor failure,--

Signed and Sealed this
Eighteenth Day of February, 2025

Coke Morgan Stewart
*Acting Director of the United States Patent and Trademark Office*